United States Patent
Devens, Jr. et al.

(10) Patent No.: US 8,048,352 B2
(45) Date of Patent: Nov. 1, 2011

(54) MEDICAL DEVICES

(75) Inventors: Douglas A. Devens, Jr., St. Paul, MN (US); Michele Zoromski, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 12/391,667

(22) Filed: Feb. 24, 2009

(65) Prior Publication Data

US 2009/0267259 A1    Oct. 29, 2009

Related U.S. Application Data

(60) Division of application No. 10/756,721, filed on Jan. 13, 2004, now abandoned, which is a continuation-in-part of application No. 10/728,079, filed on Dec. 4, 2003, now abandoned.

(51) Int. Cl.
*B29C 47/06* (2006.01)
*B29D 23/00* (2006.01)
*A61M 25/00* (2006.01)

(52) U.S. Cl. ......... 264/171.27; 264/171.28; 264/173.12; 264/173.14; 264/173.16; 264/173.19; 428/36.91; 604/93.01

(58) Field of Classification Search ............... 428/34.1, 428/34.4, 34.5, 34.6, 34.7, 35.2, 35.7, 36.4, 428/36.8, 36.9, 36.91, 36.92; 264/464, 471, 264/171.26, 171.27, 171.28, 173.12, 173.14, 264/173.15, 173.16, 173.19; 604/93.01

See application file for complete search history.

(56) References Cited

U.S. PATENT DOCUMENTS

| | | | |
|---|---|---|---|
| 3,752,617 A | 8/1973 | Burlis et al. |
| 3,767,538 A | 10/1973 | Politycki et al. |
| 4,211,741 A | 7/1980 | Ostoich |
| 4,627,844 A | 12/1986 | Schmitt |
| 4,652,663 A | 3/1987 | Takago et al. |
| 4,963,313 A | 10/1990 | Noddin et al. |
| 5,195,969 A | 3/1993 | Wang et al. |
| 5,270,086 A | 12/1993 | Hamlin |
| 5,320,100 A | 6/1994 | Herweck et al. |
| 5,714,110 A | 2/1998 | Wang et al. |
| 5,797,877 A | 8/1998 | Hamilton et al. |

(Continued)

FOREIGN PATENT DOCUMENTS

EP    1 344 549 A1    9/2003

(Continued)

OTHER PUBLICATIONS

Devens, Jr. et al., U.S. Appl. No. 10/728,079, filed Dec. 4, 2003.

(Continued)

*Primary Examiner* — Walter B Aughenbaugh
(74) *Attorney, Agent, or Firm* — Seager, Tufte & Wickhem, LLC

(57) ABSTRACT

Medical devices and methods of making the devices are described. In some embodiments, the methods include a method of manufacturing a device including a first layer and a second layer, the method including the steps of selecting a material for the second layer, the material having a viscosity value at a shear rate of about $1\ s^{-1}$ or less and at a selected temperature; selecting a nanocomposite material for the first layer that has a viscosity within about 20% to about 125% of the viscosity value of the material for the second layer; and co-extruding the first and second layers.

18 Claims, 6 Drawing Sheets

U.S. PATENT DOCUMENTS

| | | | |
|---|---|---|---|
| 5,853,886 A | | 12/1998 | Pinnavaia et al. |
| 5,877,248 A * | | 3/1999 | Beall et al. ............... 524/450 |
| 5,951,494 A | | 9/1999 | Wang et al. |
| 5,962,553 A | | 10/1999 | Ellsworth |
| 6,120,361 A | | 9/2000 | Konishi et al. |
| 6,149,997 A | | 11/2000 | Patel et al. |
| 6,165,166 A | | 12/2000 | Samuelson et al. |
| 6,210,364 B1 | | 4/2001 | Anderson et al. |
| 6,319,228 B1 | | 11/2001 | Kastenhofer |
| 6,423,768 B1 | | 7/2002 | Khouri |
| 6,431,219 B1 | | 8/2002 | Redler et al. |
| 6,447,860 B1 * | | 9/2002 | Mueller et al. ............... 428/36.6 |
| 6,464,683 B1 | | 10/2002 | Samuelson et al. |
| 6,488,694 B1 | | 12/2002 | Lau et al. |
| 6,503,224 B1 | | 1/2003 | Forman et al. |
| 6,595,952 B2 | | 7/2003 | Forsberg |
| 6,946,092 B1 | | 9/2005 | Bertolino et al. |
| 7,166,099 B2 | | 1/2007 | Devens, Jr. |
| 7,517,353 B2 * | | 4/2009 | Weber ............... 606/200 |
| 2002/0120049 A1 | | 8/2002 | Van Es et al. |
| 2002/0161096 A1 | | 10/2002 | Loontjens et al. |
| 2003/0050686 A1 | | 3/2003 | Rader-Devens et al. |
| 2003/0093107 A1 | | 5/2003 | Parsonage et al. |
| 2003/0141625 A1 | | 7/2003 | Shelby et al. |
| 2004/0186377 A1 | | 9/2004 | Zhong et al. |
| 2005/0124976 A1 | | 6/2005 | Devens, Jr. et al. |

FOREIGN PATENT DOCUMENTS

| | | |
|---|---|---|
| JP | 57-83551 A | 5/1982 |
| WO | 93/11190 A1 | 6/1993 |
| WO | 01/32398 A1 | 5/2001 |
| WO | 01/34685 A1 | 5/2001 |
| WO | 02/36194 A2 | 5/2002 |
| WO | 03/026532 A2 | 4/2003 |

OTHER PUBLICATIONS

Bertolino et al., U.S. Appl. No. 09/950,195, filed Oct. 10, 2001.

Bird, R. Byron et al., "Material Functions for Poymeric Liquids," Dynamics of Polymeric Liquids, vol. 1, Chap. 3, John Wiley & Sons, Inc. (1987) pp. 99-168.

Cox, W.P. et al., "Correlation of Dynamic and Steady Flow Viscosities," Journal of Polymer Science, vol. XXVIII, No. 118 (1958) pp. 619-622.

Kossovsky, N. et al., "Conformationally Stabilizing Self-Assembling Nanostructured Delivery Vehicles for Biochemically Reactive Pairs," Nanostructured Materials, vol. 5, No. 2 (1995) pp. 233-247.

Hawley's Condensed Chemical Dictionary, 14th Edition, entry for "viscosity", John Wiley & Sons, Inc., 2002.

* cited by examiner

MEDICAL DEVICES

CROSS-REFERENCE TO RELATED APPLICATIONS

This application is a divisional of U.S. application Ser. No. 10/756,721, filed Jan. 13, 2004, now abandoned, which is a continuation-in-part of U.S. application Ser. No. 10/728,079, filed on Dec. 4, 2003, now abandoned, the entire disclosures of which are both incorporated by reference.

TECHNICAL FIELD

The invention relates to medical devices, such as, for example, medical tubing, guide wires, catheters, and balloon catheters, and methods of making the devices.

BACKGROUND

Intravascular medical devices, such as guide wires, catheters, and medical tubing, allow physicians to perform a medical procedure, such as balloon angioplasty or delivery of an endoprosthesis, e.g., a stent. In some cases, a device is inserted into a patient's vascular system at a convenient site and subsequently delivered, e.g., pushed, through the vascular system to a target site. The path that the device takes through the vascular system to the target site can be relatively tortuous, for example, requiring the device to change direction frequently.

In some circumstances, it is desirable for the device to have relatively good flexibility so that it can track along the tortuous path. At the same time, the device preferably has good pushability so that forces applied proximally to the device can be transmitted distally to deliver the device.

SUMMARY

The invention relates to medical devices, such as, for example, catheters, stents, and medical tubing.

In one aspect, the invention features a co-extruded medical tube including a first layer, and a second layer disposed radially inwardly of the first layer, wherein the first and second layers have different compositions, and one of the layers has a nanocomposite material and has a viscosity between 25% and 120% of a viscosity of the other layer as measured at a shear rate of 1 $s^{-1}$ and a temperature of 220° C.

Embodiments may include one or more of the following features. The second layer is bonded directly to the first layer. The first layer is the outermost layer of the co-extruded tube. The composition of the first layer is a nanocomposite. The composition of the second layer is a non-nanocomposite. The first and second layer have a thickness uniformity of 80% or greater around the circumference of the medical tube.

The medical tube can further include a third layer, e.g., one having a different composition than the second layer. The third layer can have a viscosity greater than a viscosity of the second layer as measured at a shear rate of 1 $s^{-1}$ and a temperature of 220° C. The composition of the third layer can be different than the composition of the first layer. The third layer can be the innermost layer.

In another aspect, the invention features a co-extruded medical tube including a first layer having a nanocomposite material having a first viscosity, and a second layer having a second material and having a second viscosity. The first viscosity is from about 25% to about 120% of the second viscosity as measured at a shear rate less than about 1 $s^{-1}$ and a temperature of about 60° C. to about 120° C. above a flow temperature of a highest flow temperature material that is co-extruded.

Embodiments may include one or more of the following features. The shear rate has a value of about 0.1 $s^{-1}$. The temperature is about 220° C. The second material includes Plexar® PX380, a modified polyolefin. The first layer is at least about 30% of a cross-sectional area of the medical tube. The second layer is at least about 5% of a cross-sectional area of the medical tube.

The medical tube can further include a third co-extruded layer having a third material having a third viscosity that varies with shear rate. The second viscosity can be from about 5% to about 35% of the third viscosity as measured at a shear rate less than about 1 $s^{-1}$ and a temperature of about 60° C. to about 120° C. above a flow temperature of a highest flow temperature material that is co-extruded. The third material can include Marlex®, a high density polyethylene. The third layer can be at least about 10% of the medical device.

The first layer and the second layer can be coextensively co-extruded or intermittently co-extruded.

In another aspect, the invention features a medical device including a tubular body having a plurality of co-extruded layers, wherein a viscosity of a first layer is from about 25% to about 120% of a second viscosity of an adjacent layer. The viscosity is measured at a shear rate less than about 1 $s^{-1}$ and a temperature of about 60° C. to about 120° C. above a flow temperature of a highest flow temperature material that is co-extruded.

Embodiments may include one or more of the following features. The shear rate is below about 0.1 $s^{-1}$. At least one of the plurality of co-extruded layers includes a nanocomposite material. The plurality of co-extruded layers includes an outer nanocomposite layer, a middle layer, and an inner layer. The middle layer includes Plexar® PX380, a modified polyolefin, and/or the inner layer includes Marlex®, a high density polyethylene.

In another aspect, the invention features a method of manufacturing a device including a first layer and a second layer. The method includes selecting a shear rate at or below about 1 $s^{-1}$, selecting a temperature, selecting a material for the second layer, the material having a viscosity value at the shear rate and the temperature, selecting a nanocomposite material for the first layer that has a viscosity within about 20% to about 125% of the viscosity value of the material for the second layer, and co-extruding the first and second layers.

Embodiments may include one or more of the following features. The device is a medical device. The shear rate is below about 0.5 $s^{-1}$, e.g., about 0.1 $s^{-1}$. The temperature is about 60° C. to about 120° C. above a flow temperature of a highest flow temperature material co-extruded.

In another aspect, the invention features a tubular member including a first layer and a second layer co-extruded with the first layer, wherein one of the layers has a nanocomposite material, and one of the layers has a thickness that varies by less than about 20% from a mean value of thickness. The thickness is measured at four points per cross-sectional cut made at ten random, non-consecutive locations along a production length of the tubular member.

Embodiments may include one or more of the following features. The thickness varies by less than about 15% (e.g., less than about 10%) from the mean value of thickness. The first layer has a first thickness that varies less than about 20% from a mean value of thickness for the first layer, and the second layer has a second thickness that varies less than about 20% from a mean value of thickness for the second layer. The tubular member further includes a third layer.

In another aspect, the invention features a method of making a medical device. The method includes forming a tubular member having a first layer and a second layer co-extruded with the first layer, and incorporating a portion of the tubular member as a component of the medical device. One of the layers has a nanocomposite material, and one of the layers has a thickness that varies by less than about 20% from a mean value of thickness. The thickness is measured at four points per cross-sectional cut made at ten random, non-consecutive locations along a production length of the tubular member.

Embodiments may include one or more of the following features. The medical device can be, for example, a catheter or a balloon-catheter. The thickness can vary by less than about 15% (e.g., less than about 10%) from the mean value of thickness.

Embodiments may have one or more of the following advantages. The medical device can have two or more layers that together provide relatively good flexibility so that the medical device can track along a tortuous path within a patient's body. At the same time, the two or more layers of the medical device provide good pushability so that forces applied proximally to the device can be transmitted distally to deliver the device. For example, at least one of the layers of the medical device includes a nanocomposite material that increases the stiffness of the medical device such that the medical device can be advanced through a patient's body without kinking and/or buckling. A medical device including a layer having nanocomposite material can be formed to have concentric multiple layers with high quality interfaces. As a result, the medical device has a relatively smooth interior surface, which does not interfere with guide wire movement and hence pushability of the medical device. As a further result, the multiple concentric layers reduce the likelihood of forming weak spots (e.g., spot that are deficient in strength) in the medical device. A medical device including multiple layers wherein at least one of the layers includes nanocomposite materials can be extruded economically, that is, scrap material is reduced because devices with concentric multiple layers can be consistently produced.

Other aspects, features and advantages of the invention will be apparent from the description of the preferred embodiments and from the claims.

DETAILED DESCRIPTION

Figure 1:
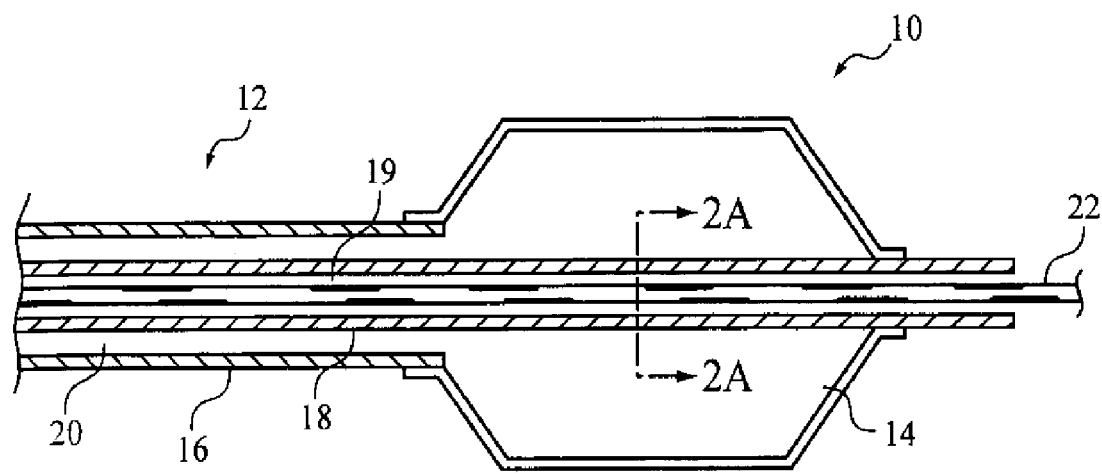
FIG. 1 is an illustration of a portion of a balloon catheter system.

Referring to FIG. 1, a balloon catheter system 10 includes a catheter 12 and an inflatable balloon 14 carried by the catheter. Catheter 12 includes an outer shaft 16 and an inner shaft 18 defining a lumen 19. Shafts 16 and 18 are concentric and define an annular lumen 20 between them. During use, catheter system 10 can be delivered to a treatment area (e.g., a coronary artery) by passing lumen 19 over a guide wire 22 emplaced in the body, and pushing the catheter system to the treatment area. Balloon 14 can then be inflated or deflated by delivering or withdrawing a fluid (such as a liquid or a gas) through annular lumen 20. Examples of balloon catheter systems are described in U.S. Pat. Nos. 5,195,969 and 5,270,086, and exemplified by the Maverick® single-operator exchange system and over-the-wire systems, available from Boston Scientific Scimed, Inc., Maple Grove, Minn.

Figure 2A:
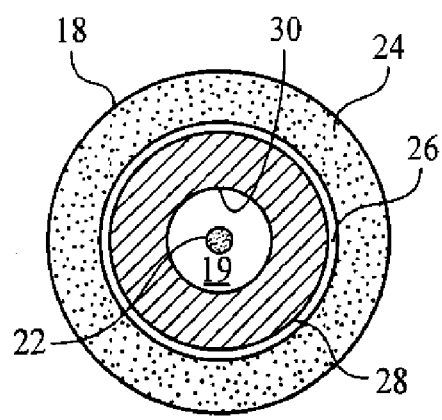
FIG. 2A is a cross-sectional view of a tube of the balloon catheter system of FIG. 1, taken along line 2A-2A.

Referring to FIG. 2A, inner shaft 18 has multiple, co-extruded polymer layers 24, 26, 28. Inner layer 28 is made of a high radial strength, low friction polymer (e.g., high density polyethylene) that minimizes the likelihood of collapse of the catheter 12 during balloon inflation and, at the same time, facilitates movement of the catheter over guide wire 22. Middle layer 26 is made of a polymer (e.g., a modified polyolefin) that enhances bonding between inner layer 28 and outer layer 24. Outer layer 24 enhances the pushability of the catheter 12, and is typically relatively stiff as compared to the inner and middle layers 28, 26, respectively. At least one of the layers, e.g. the outer layer 24, is made out of a nanocomposite material. The nanocomposite material can include nanosized (e.g., 1000 nm to 1 nm) particles (such as clay, glass, or carbon particles) dispersed within a polymer matrix (such as a polyamide available as Nylon 12® from DuPont deNemours & Co, Wilmington, Del.). The addition of the nanosized particles enhances the mechanical properties, such as the stiffness of the polymer.

Figure 2B:
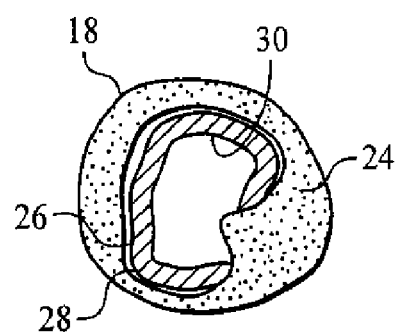
FIG. 2B is a cross-sectional view of a tube of a balloon catheter system that has non-uniform co-extruded layers.

As illustrated in FIG. 2A, the uniformity of the co-extruded layers is maintained. The thickness of the layers is substantially constant around the circumference of catheter 12 and adjacent layers are separated by an interface. The high precision with which layers 24, 26, 28 can be formed means that inner shaft 18 can be formed accurately and consistently, which in turn can enhance the performance and manufacture of catheter system 10 (e.g., by reducing scrap). Referring to FIG. 2B, in a non-uniform co-extrusion, one polymer layer blends into adjacent layers on occasion. The irregularity of this co-extrusion affects the performance of the catheter by, e.g., modifying the flexibility and kink-resistance of the tube, varying its inner or outer diameter, and/or exposing an outer polymer layer to the guide wire lumen, which could be non-optimal for low friction sliding over a guide wire. In embodiments, the precision of the co-extrusion can be such that the layers have a thickness uniformity of about 80% or greater (e.g., equal to or greater than 85%, equal to or greater than 90%, or equal to or greater than 95%) around the circumference over a length of a catheter that is 60 centimeters or greater.

The precision of the co-extrusion of a three-layered tube including a nanocomposite material is controlled by selecting combinations of materials that are compatible under certain shear rate characteristics. In some embodiments, the nanocomposite material is selected to have viscosities, under certain shear rate characteristics, that are compatible with materials used to form middle layer 26 (i.e., the layer used to bind the inner layer to the outer layer). For example, the nanocomposite material can have a viscosity that is within about 25% to about 120% of the viscosity of the middle layer as measured at a shear rate at or below 1 s$^{-1}$ and a temperature of 220° C. That is, the viscosity of the nanocomposite material can be greater than or equal to about 25%, greater than or equal to about 30%, greater than or equal to about 35%, greater than or equal to about 40%, greater than or equal to about 45%, greater than or equal to about 50%, greater than or equal to about 55%, greater than or equal to about 60%, greater than or equal to about 65%, greater than or equal to about 70%, greater than or equal to about 75%, greater than or equal to about 80%, greater than or equal to about 85%, greater than or equal to about 90%, greater than or equal to about 95%, greater than or equal to about 100%, greater than or equal to about 105%, greater than or equal to about 110%, greater than or equal to about 115% of the middle layer 26; and/or equal to or less than 120%, equal to or less than 115%, equal to or less than 110%, equal to or less than 105%, equal to or less than 100%, equal to or less than 95%, equal to or less than 90%, equal to or less than 85%, equal to or less than 80%, equal to or less than 75%, equal to or less than 70%, equal to or less than 65%, equal to or less than 60%, equal to or less than 55%, equal to or less than 50%, equal to or less than 45%, equal to or less than 40%, equal to or less than 35%, equal to or less than 30% of the middle layer 26.

Figure 3:
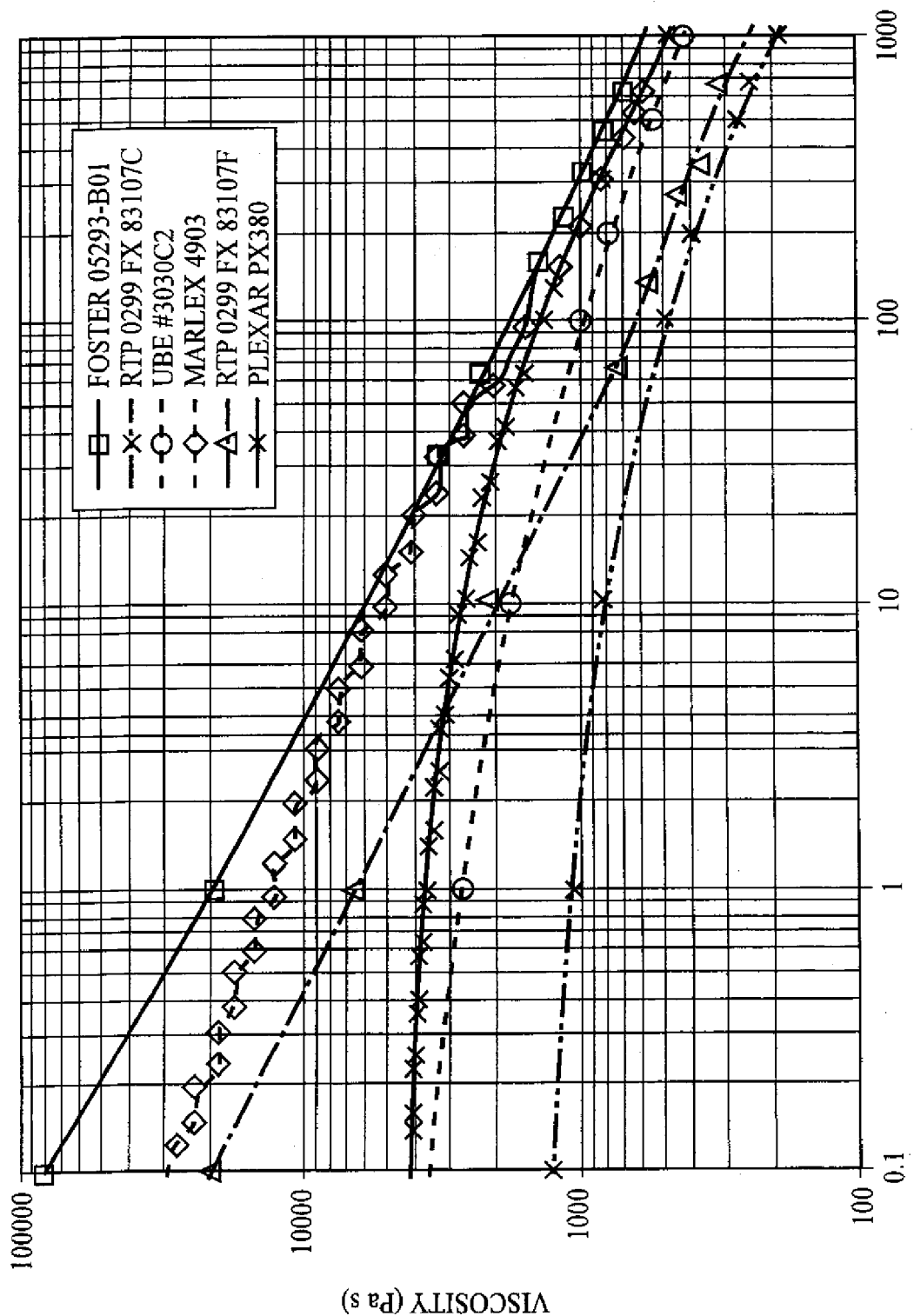
FIG. 3 is a plot of viscosity versus shear rate for several nanocomposite and pure polymer materials. The viscosity measurements in this plot were measured at a temperature of 220° C.

Referring to FIG. 3, in embodiments, the nanocomposite material exhibits a viscosity profile as a function of shear rate in which the viscosity tends toward a maximum. Certain nanocomposite materials, such as Foster nanocomposite formula number 05293-B01 available from Foster Compounding, Dayville, Conn. and RTP formula number 0299 FX 83107F available from RTP Company, Winona, Minn., have a viscosity profile that tends toward infinity at a low shear rate. Other nanocomposite materials have a viscosity profile that tends towards a maximum viscosity at low shear rate values (e.g., Ube Nano-PA 12 formula number 3030C2 available from Ube Industries, Ube America Inc., New York, N.Y. and RTP formula number 0299 FX 83107C available from RTP Company, Winona, Minn.), which is more common to pure polymers and are typically more compatible with other materials for precision co-extrusion.

Materials used to form the middle layer 26 have viscosities that are lower than viscosities of materials used in the inner layer 28 at low shear rates (e.g., at or below 1 s$^{-1}$). In certain embodiments, the middle layer 26 has a viscosity that is 5% to 35% of the viscosity of the inner layer 28. For example, the viscosity of middle layer 26 can be greater than or equal to about 5%, greater than or equal to about 10%, greater than or equal to about 15%, greater than or equal to about 20%, greater than or equal to about 25%, greater than or equal to about 30% of inner layer 28; and/or less than or equal to about 35%, less than or equal to about 30%, less than or equal to about 25%, less than or equal to about 20%, less than or equal to about 15%, less than or equal to about 10% of the inner layer 28. It is believed that a lower viscosity material aids in the co-extrusion of a higher viscosity material by acting as a lubricant to minimize frictional forces along the extrusion channel. For example, in oil pipelines, water (a low viscosity material) is commonly used to aid the flow of oil (a high viscosity material) through the pipe. As a result of using a middle layer with a lower viscosity than the inner layer, flow within a co-extrusion device is increased, thereby further increasing the likelihood of precision co-extrusion.

The viscosity of a material can be experimentally determined by capillary or parallel plate rheometry. In capillary rheometry, a material (e.g., a polymer or a nanocomposite) is placed within a capillary rheometer (e.g., Kayness Incorporated, Galaxy V, Model 1802) at about room temperature. The capillary rheometer is heated to a target temperature about 80° C. above the flow temperature of the material, and held at the target temperature for about 10 minutes. The flow temperature is the temperature at which the material transforms from a solid state to a liquid state, for example the melt temperature for crystalline polymers and the glass transition temperature for non-crystalline polymers. The flow temperature of the material can be determined by differential scanning calorimetry (DSC) (e.g., using a Thermal Analysis Model 2920). In cases in which DSC reveals more than one flow temperature, such as when the material includes a blend of polymers, the highest of the flow temperatures is used as the flow temperature of the material in heating the rheometer. Next, the material is extruded using a pressure at which the shear rate has a constant value, such as 100 s$^{-1}$. The rheometer then calculates and reports the viscosity of the material at the selected constant shear rate in accordance with ASTM 3835-96.

The viscosity of a material can also be measured using a parallel plate rheometer (i.e., dynamic shear measurement) using a method described by ASTM D4065-95 (Vol. 8.02) and ASTM D4440-95a (Vol. 8.03). The data line measured using the parallel plate rheometer is fit using either the Power Law Model or the Ellis Model, depending upon the rheological characteristics of the polymer being measured. To compute the viscosity, the data is transformed using the Cox-Merz rule to steady viscosity calculations, such as those produced by a capillary rheometer. The Cox-Merz rule is described in detail on p. 150 of *Dynamics of Polymer Liquids*, Vol. 1, 2$^{nd}$ Edition, by Bird et al., published by John Wiley and Sons, New York, as well as on pages 619-622 of the *Journal of Polymer Science*, Vol. 28, 1958. As indicated above, viscosity can be measured by either capillary or parallel plate rheometry. To the extent values by the two techniques are not in agreement, it is typically sufficient that one or the other provides a viscosity value that satisfies the relationship for high precision extrusions, as discussed above. While either technique can be used to measure viscosity, typically, viscosity measurements at low shear rates (below about 1 s$^{-1}$) are measured using the parallel plate method.

Figures 4A, 4B:
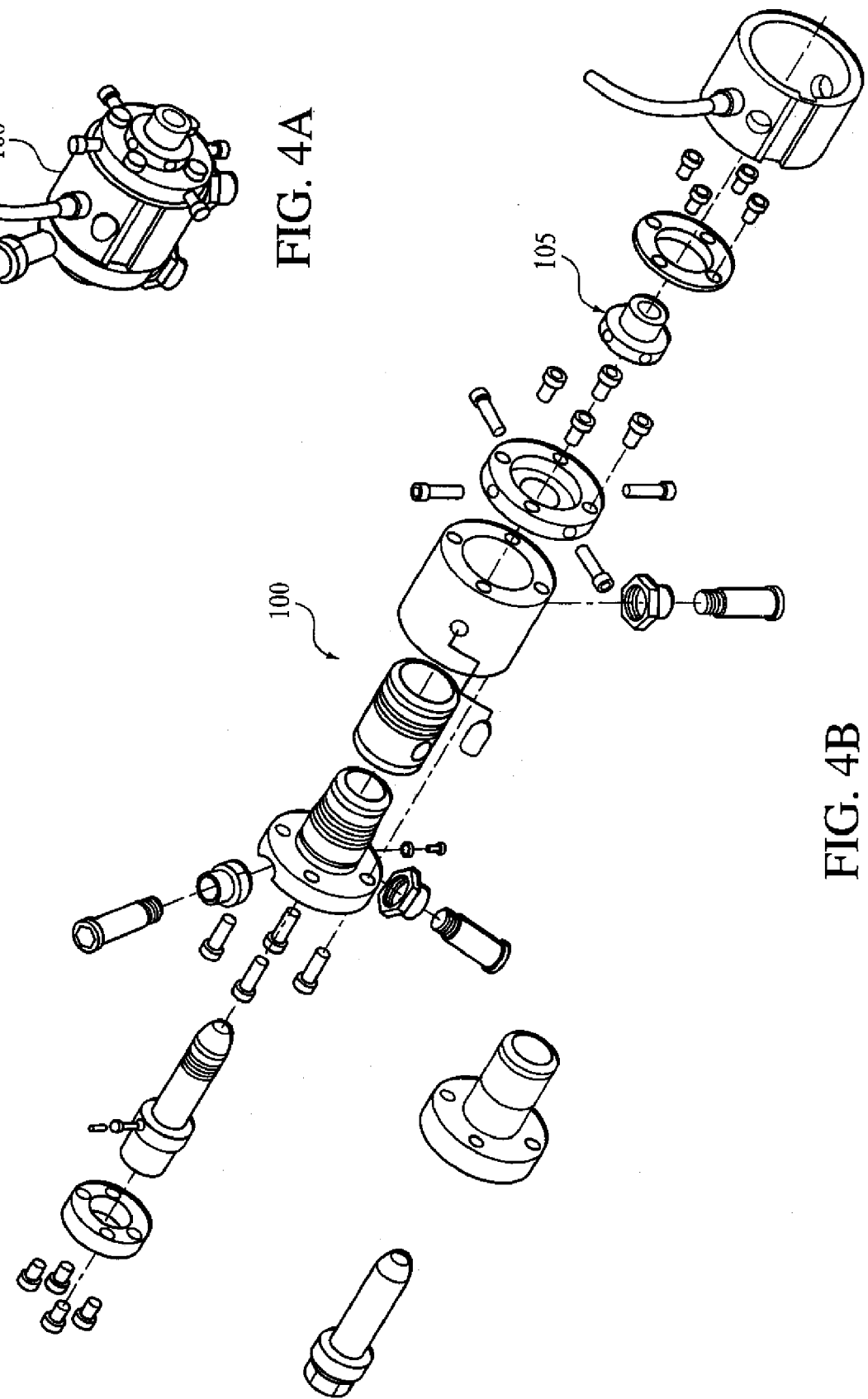
FIG. 4A is a perspective view of an exemplary cross-head device.
FIG. 4B is an exploded view of the cross-head device of FIG. 4A.
Figure 5A:
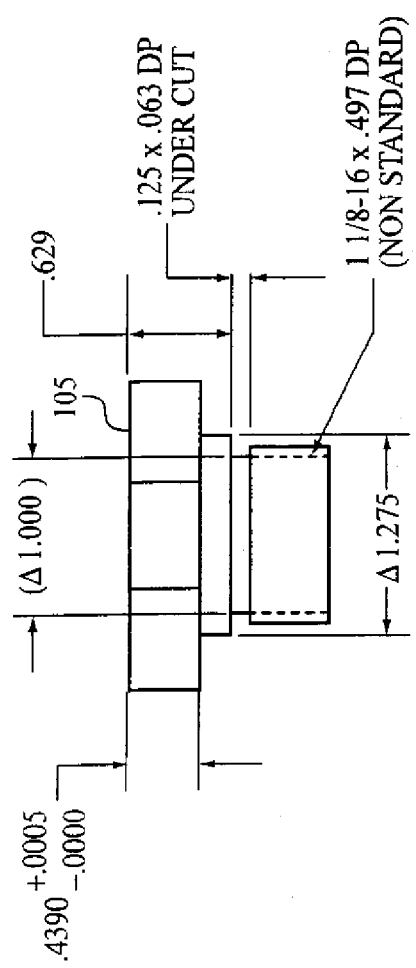
FIG. 5A is a side view of an exemplary retainer nut used within the cross-head device of FIG. 4A.
Figure 5C:
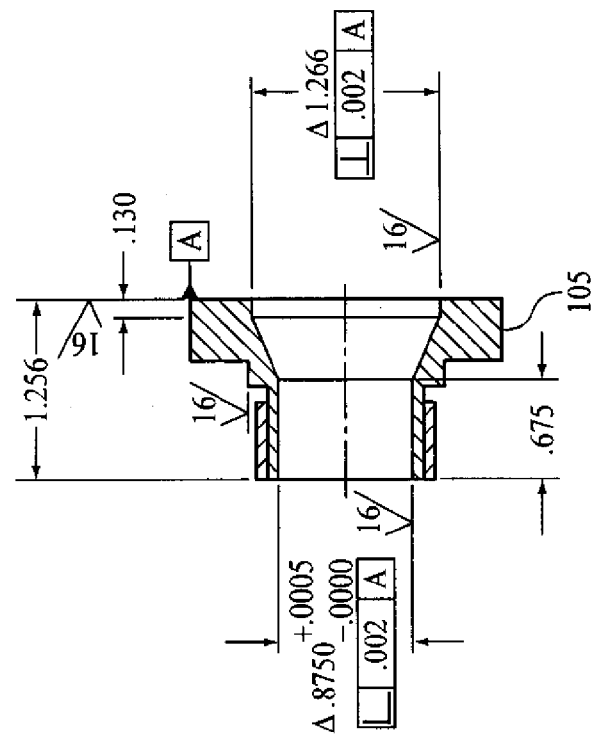
FIG. 5C is a cross-sectional view of the retainer nut taken along line 5C-5C in FIG. 5B.
Figure 5B:
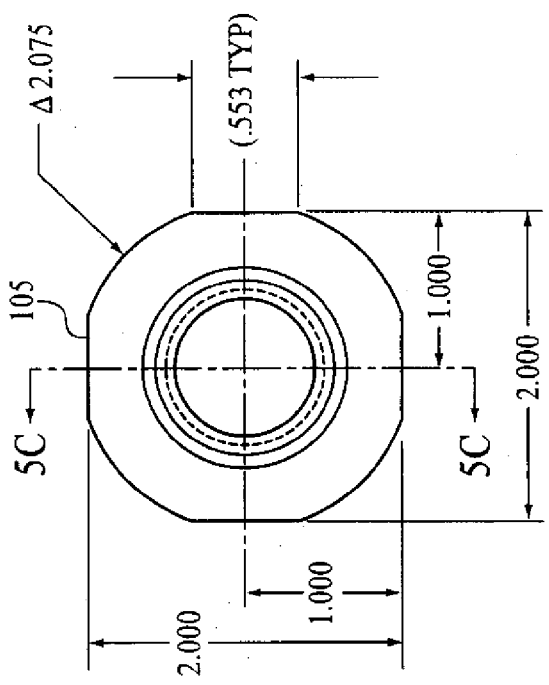
FIG. 5B is a top view of the retainer nut of FIG. 5A.

After the materials for each layer are selected based on their material properties (e.g., stiffness or lubricity) and good combination of shear viscosities at a low shear rate, the materials are used to form a co-extruded product, e.g., a tube. For example, a tube can be prepared by using an extrusion apparatus such as, for example, one having a cross-head, such as cross-head 100 shown in FIGS. 4A and 4B and exemplified by a cross-head device manufactured by GENCA (St. Petersburg, Fla.), model number B1 Tri Die. To aid in attachment (i.e., less time to assemble and disassemble) of cross-head 100 to an extruder such as, for example, an extruder commercially available from CW Brabender, South Hackensack, N.J., a retainer nut 105 formed from 440C stainless steel, as shown in FIGS. 5A, 5B, and 5C was used. Illustrative examples, including process parameters, for making a co-extruded product are provided below. Other illustrative examples of process parameters, techniques and apparatus for extruding a three-layered tube can be found in U.S. Pat. No. 6,165,166 issued to Samuelson et al., U.S. Pat. No. 6,319,228 issued to Kastenhofer, and U.S. Pat. No. 6,464,683 issued to Samuelson et al., the disclosures of which are hereby incorporated by reference.

In some embodiments, melt pumps are used to modulate the feed rate or flow of polymers in the crosshead. Exemplary melt pumps are described in International Application Publication Number, WO 01/32398, entitled "Method and Apparatus for Extruding Catheter Tubing", the disclosure of which is hereby incorporated by reference. In certain embodiments servo-controlled valves are used to modulate the feed rate or to flow of polymers in the crosshead. Exemplary servo-controlled valves are described in U.S. Pat. No. 3,752,617 issued to Burlis et al, the disclosure of which is hereby incorporated by reference.

Figure 6:
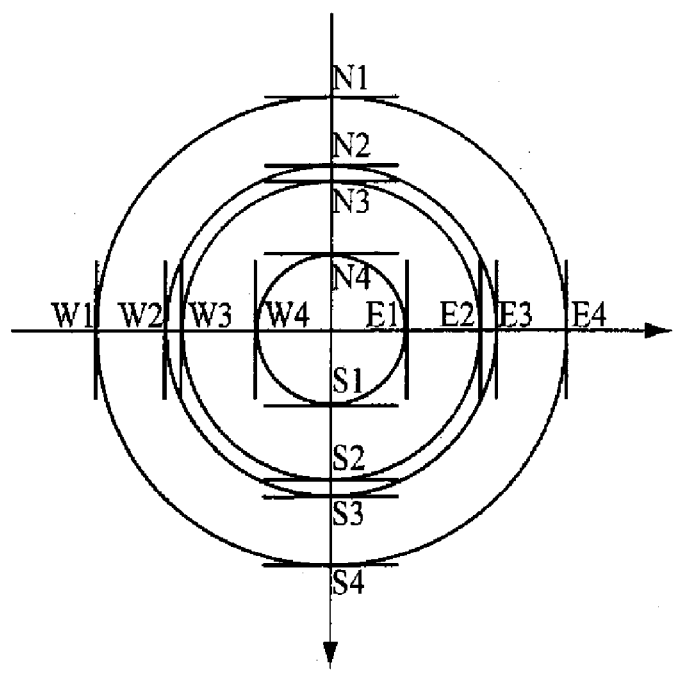
FIG. 6 is a cross-sectional view of a multilayer tube.
Figure 7:
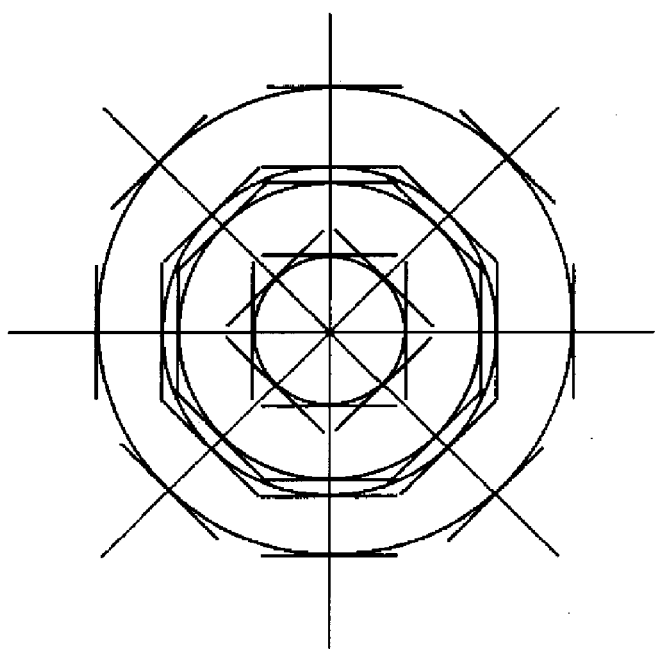
FIG. 7 is a cross-sectional view of a multilayer tube.

By screening the materials for certain combinations of shear viscosities at low shear rates, the co-extruded product can be formed having well-defined features. In embodiments in which the co-extruded product is a tube, the tube has a radial cross section with good concentricity, e.g., the thickness of each layer is accurate and precise. Referring to FIGS. 6 and 7, the concentricity of the tube can be determined by examining the radial cross section of the tube, and measuring the thickness of each layer (as shown, three layers) along four equally spaced directions (FIG. 6) or eight equally spaced directions (FIG. 7). The thickness can be measured, for example, using a microscope (e.g., a Toolscope microscope model number MM-40/2, available from Nikon, Melville, N.Y.) and a digital caliper or a micrometer. The layers are considered concentric when the thickness of each layer varies by no more than about 20% (e.g., less than or equal to about 15%, 10%, or 5%) from a mean value of thickness measured around its circumference for a sampling over the length of a production run. A sampling over the length of a production run is conducted by selecting 10 or more (e.g., 10, 15, or 20) random, non-consecutive points along a production run length (e.g., 1000 feet) and measuring the thickness of each layer at each of the 10 points.

The co-extruded concentric inner tube can then be incorporated into catheter system 10. For example, inner tube 18 can be attached to balloon 14 using an adhesive or a weld, such as, for example, a radio-frequency weld or a laser weld. Catheter system 10 can be used, for example, for angioplasty and/or to deliver an endoprosthesis, such as a stent.

Turning now to the materials for the layers, as indicated above, in certain embodiments, one (or more) layers of the co-extruded product includes a nanocomposite material. The nanocomposite material can include a polymer matrix having dispersed therein nanosized (e.g., 1000 nm to 1 nm) particles that enhance the properties (e.g., strength and stiffness) of the polymer. Examples of nanocomposite materials include Ube Nano-PA12 (formula number #3030C2, available from Ube Industries, Ube America Inc., New York, N.Y.); RTP formula number 0299 FX 83017C, (available from RTP Company, Winona, Minn.). Other examples of nanocomposite materials are described in U.S. Patent Pub. No. 2003/0065355. In certain embodiments, the nanocomposite material has a shear viscosity of about 500 to about 15,000 Pa-s (e.g., about 500 to about 2,500 Pa-s) at a shear rate of or below $1\ s^{-1}$ (e.g., $1\ s^{-1}$, $0.5\ s^{-1}$, $0.1\ s^{-1}$) at about 380° F. to about 450° F.

The particles in the nanocomposite material can be synthetic or natural. Examples of particles include phyllosilicates, including clays and micas (that may optionally be intercalated and/or exfoliated) such as montmorillonite (mmt), hectorites, hydrotalcites, vermiculite, and laponite; monomeric silicates such as polyhedral oligomeric silsesquioxanes (POSS) including various functionalized POSS and polymerized POSS; single and multi walled carbon and ceramic nanotubes, nanowires and nanofibers including single and multi walled fullerene nanotubes, silica nanogels, and alumina nanofibers; metal and metal oxide powders including aluminum oxide, titanium oxide, tungsten oxide, tantalum oxide, zirconium oxide, gold (Au), silver (Ag), platinum (Pt) and magnetic or paramagnetic powders such as neodymium iron boron, superparamagnetic ferrite oxide or superparamagnetic maghemite; organic materials, including temperature sensitive polymers such as polyvinylpyrrolidone and n-isopropylacrylamide copolymers or blends, and poloxamer. Biodegradable polymers may also be used, may be magnetized, if desired, and include for example, poly(lactic) acid, polysaccharide, and polyalkycyanoacrylate. A nanocomposite material can include a mixture of two or more different particles, in any combination. A nanocomposite material can include, for example, about 0.1 to about 10 weight percent of particles.

Exemplary polymer matrix materials for a nanocomposite material include thermoplastics and thermosets. Examples of thermoplastics include, for example, polyolefins, polyamides, such as nylon 12, nylon 11, nylon 6/12, nylon 6, and nylon 66, polyesters, polyethers, polyurethanes, polyureas, polyvinyls, polyacrylics, fluoropolymers, copolymers and block copolymers thereof, such as block copolymers of polyether and polyamide, e.g., Pebax®; and mixtures thereof. Examples of thermosets include elastomers such as EPDM, epichlorohydrin, nitrile butadiene elastomers, silicones, etc. Conventional thermosets such as expoxies, isocyanates, etc., can also be used. Biocompatible thermosets, for example, biodegradable polycaprolactone, poly(dimethylsiloxane) containing polyurethanes and ureas, and polysiloxanes, may also be used. One or more of these materials can be used in the nanocomposite material, in any combination.

Other embodiments of nanocomposite materials are described in Parsonage et al., U.S. Patent Pub. No. 2003/0093107, hereby incorporated by reference in its entirety. For example, the nanocomposite materials can be functionalizers to enhance the properties of the materials and/or to enhance compatibility between layers. The nanocomposite materials can include one or more coupling or compatibilizing agents.

One or more non-nanocomposite polymers, e.g., pure polymers, can be used in the other layers of the co-extruded product. In embodiments, one or more layers include a high density polyethylene, such as Marlex® 4903 available from Chevron Phillips Chemical Company, Woodlands, Tex. In embodiments, one or more layers can include a modified polyolefin, such as a maleic anhydride polyolefin available as Plexar® PX380 from Equistar Chemical Company, Newark, N.J.). In certain embodiments, one or more layers can contain one or more nylons. Examples of nylons include aliphatic nylons, such as Nylon 11 (Elf Atochem), Nylon 6 (Allied Signal), Nylon 6/10 (BASF), Nylon 6/12 (Ashley Polymers) and Nylon 12. Additional examples of nylons include aromatic nylons, such as GRIVORY®(EMS) and Nylon MXD-6. Other nylons and/or combinations of nylons can be used.

In some embodiments, one or more layers can contain a liquid crystal polymer (LCP) (e.g., a composite material having the LCP incorporated therein). Examples of LCPs include polyester(s), polyamide(s) and/or their copolymers, such as VECTRA® A (Ticona), VECTRA® B (Ticona) and VECTRA® LKX (Ticona) (e.g., VECTRA® LKX 1111 (Ticona)). Other LCPs and/or combinations of LCPs can be used.

In certain embodiments, an adhesion enhancing material can be incorporated into one or more material layers. An adhesion enhancing material can be used, for example, to enhance the adhesion between adjacent layers. Examples of adhesion enhancing materials include epoxy or anhydride modified polyolefins, such as LOTADER® (Elf Atochem) and KODAR® PETG (Eastman Kodak). An adhesion enhancing material can be added to a material (e.g., a composition containing one or more polymers) prior to extrusion (described below). For example, in embodiments in which alternate layers are formed of PET and PBT, PETG can be added to the PET before extrusion.

The amount of adhesion enhancing material can vary depending upon the intended use. In some embodiments, a sufficient amount of adhesion enhancing material(s) are included in the material so that the adhesion enhancing material(s) makes up at least about 0.5 percent of the resulting mixture that forms the layer (e.g., at least about 1 percent, at least about 5 percent, at least about 10 percent) and/or at most about 20 percent of the resulting mixture that forms the layer (e.g., at most about 15 percent, at most about 12 percent, at most about 10 percent).

In certain embodiments, the adhesion between one or more adjacent layers can vary as layer thickness is varied. Generally, embodiments can provide adhesion between one or more (e.g., all) layers in a medical device (e.g., a tube). For example, one or more (e.g., all) layers in a medical device (e.g., a tube) can demonstrate good adhesion when flexed, deflated and/or inflated. In some embodiments, a medical device (e.g., a tube) can show good flexibility and/or adhesion (e.g., when one or more layers are relatively thin).

In some embodiments, a compatibilizing material can be incorporated into one or more material layers. The compatibilizing material can be designed, for example, to modify one or more phase boundaries of the LCP(s) and one or more of the other polymer(s) (e.g., thermoplastic polymer(s)) and/or to enhance adhesion between the LCPs and one or more of the other polymer(s). The compatibilizing material can also be designed to enhance adhesion between nanocomposites material and the polymer(s). The compatibilizing material can be a copolymer, such as a block copolymer, including moieties of at least two different chemical structures, respectively providing compatibility with an LCP and one or more other polymers in the mixture. The compatibilizing material can be a reactive polymer that reacts with the LCP and/or one or more other polymers in the mixture. The compatibilizing material can be a catalyst that promotes a reaction between the LCP and one or more other polymers in the mixture. Other compatibilizing materials can be used. Combinations of compatibilizing materials can be used.

Examples of compatibilizing materials include copolyester elastomers, ethylene unsaturated ester copolymers, such as ethylene-maleic anhydride copolymers, copolymers of ethylene and a carboxylic acid or acid derivative, such as ethylene-methyl acrylate copolymers, polyolefins or ethylene-unsaturated ester copolymers grafted with functional monomers, such as ethylene-methyl acrylate copolymers, copolymers of ethylene and a carboxylic acid or acid derivative, such as ethylene-methyl acrylate maleic anhydride terpolymers, terpolymers of ethylene, unsaturated ester and a carboxylic acid or acid derivative, such as ethylene-methyl acrylate-methacrylic acid terpolymers, maleic acid grafted styrene-ethylene-butadiene-styrene block copolymers, and acrylic acid elastomers, such as acrylic rubbers. Similar polymers containing epoxy functional groups, for instance derived from glycidyl methylacrylate (e.g., alkyl(meth)acrylate-ethylene-glycidyl(meth)acrylate polymers) can be used. Ionomeric copolymers can be used. PETG can be used. Examples of compatibilizing materials include HYTREL® HTR-6108, POLYBOND® 3009 (BP Chemicals), SP 2205 (Chevron), DS 1328/60 (Chevron), LOTADER®W 2400, ESCOR® ATX-320, ESCOR® ATX-325, VAMAC® G1 and LOTADER® AX8660. In certain embodiments, a compatibilizing material (e.g., PETG) can be mixed with one or more polymers (e.g., an LCP-containing material) prior to extrusion.

While certain polymers and polymer combinations are discussed above, other polymers and polymer combinations can also be used. Other polymers include, for example, elastomers such as thermoplastic elastomers and engineering thermoplastic elastomers, such as polybutylene terephthalate-polyethene glycol block copolymers, which are available, for example, as HYTREL®. These are discussed in U.S. Pat. No. 5,797,877 to Hamilton, the entire content of which is incorporated herein by reference. Other polymers include polyurethanes. Other polymers include copolymers such as ABS (acrylonitrile-butadiene-styrene), ABS/nylon, ABS/polyvinyl chloride (PVC), ABS/polycarbonate, acrylonitrile copolymer, polyacrylamide, polyacrylate and polyacrylsulfone, polyesters such as polyethylene terephthalate (PET), polybutylene terephthalate (PBT), polyethylene naphthalate (PEN), liquid crystal polymer (LCP), polyester/polycaprolactone and polyester/polyadipate; and high melt temperature polyethers including polyetheretherketone (PEEK), polyethersulfone (PES), polyetherimide (PEI) and polyetherketone (PEK), polymethylpentene, polyphenylene ether, polyphenylene sulfide, and styrene acrylonitrile (SAN), ethylene, propylene ethylene vinylacetate and ethylene vinyl alcohol (EVA), various ionomers, polyethylene type I-IV, polyolefins, polyurethane, polyvinyl chloride, and polysiloxanes (silicones). Those with low to medium melt temperatures include fluorocarbons such as polychlorotriethylene (CTFE), poly[ethylene-co-chlorotrifluoroethylene] (ECTFE) copolymer ethylene tetrafluoroethylene (ETFE), copolymer tetrafluoroethylene and hexafluoropropylene (FEP), perfluoroalkane (PFA) and poly[vinylidene fluoride] (PVDF).

Other Embodiments

Inner tube 18 can include any number of layers (e.g., two layers, three layers, four layers, five layers, six layers or more). Preferably, the viscosity (measured at a shear rate of about 1 $s^{-1}$ or less and a temperature of 220° C.) of a nanocomposite layer is between about 25% and 120% a viscosity (measured at a shear rate of about 1 $s^{-1}$ or less and a temperature of 220° C.) of an adjacent layer (i.e., contacting layer such as middle layer 26, as shown in FIG. 2D).

Any one or more of the layers can be formed from one or more nanocomposites materials, in any combination. The layers can be coextensive or intermittent. For example, one or more layers of material can terminate along the length of the medical device, and optionally, extend again, spaced from where the layer terminated. One or more layers can have variable thickness. Embodiments of tubes having intermittent layer(s) and/or layer(s) of variable thickness are described in U.S. Ser. No. 10/645,014, entitled "Multilayer Medical Devices" and filed on Aug. 21, 2003, hereby incorporated by reference.

In other embodiments, the co-extruded tube and/or the methods described herein can be used to form other medical devices. For example, a co-extruded tube can be used to manufacture a medical balloon. The balloon can be made using a blow molding process in which the tube (e.g., inner shaft 18) is placed (e.g., centered) in a preheated balloon mold, and air is introduced into the tube to maintain the patency of the tube lumen. After soaking at a predetermined temperature and time, the tube is stretched for a predetermined distance at a predetermined time, rate, and temperature. The pressure inside the tube is then sufficiently increased to radially expand the tube inside the mold to form the balloon. The formed balloon can be heat treated, for example, to enhance folding memory, and/or folded into a predetermined profile. The balloon can then be attached to a catheter to form a balloon catheter. Illustrative methods of forming a balloon from a tube are described in, for example, commonly-assigned U.S. Ser. No. 10/263,225, filed Oct. 2, 2002, and entitled "Medical Balloon"; U.S. Pat. No. 6,210,364 to Anderson; U.S. Pat. No. 5,714,110 to Wang; and U.S. Pat. No. 4,963,313 to Noddin, all hereby incorporated by reference in their entirety.

The co-extruded tube described above can be formed into a guide wire, e.g., a polymer guide wire. Methods of making a guide wire, including one having good pushability is described in U.S. Pat. No. 5,951,494, hereby incorporated by reference in its entirety.

The co-extruded tube can be used as a synthetic vascular graft. The graft can be used to replace a damaged or dysfunctional body vessel (e.g., at the site of an aneurysm or an occlusion), to bypass or divert blood flow around a damaged region, or to create a shunt between an artery and a vein (e.g., for multiple needle access for hemodialysis access). Vascular grafts are described, for example, in U.S. Pat. No. 5,320,100.

The co-extruded tube can be used as a graft in a stent-graft, or a covered stent. The graft can include a nanocomposite layer for strength, and another layer carrying a drug.

The co-extruded tube can be sized and shaped to form a variety of catheters. Examples of catheters include guide catheters (e.g., as described in U.S. Pat. No. 6,595,952), tumor ablation catheters, aneurysm catheters, urology catheters, and perfusion catheters (e.g., as described in U.S. Pat. No. 6,503,224). The tube can be formed into an introducer sheath or a restraining sheath for a stent delivery system, for example, as described in U.S. Pat. No. 6,488,694. The catheters can include one or more nanocomposite layers for strength, and one or more layers carrying a marker for fluoroscopic, ultrasound, and/or magnetic resonance detection, as described, for example, in commonly assigned U.S. Ser. No. 10/390,202, filed Mar. 17, 2003.

Figure 8A:
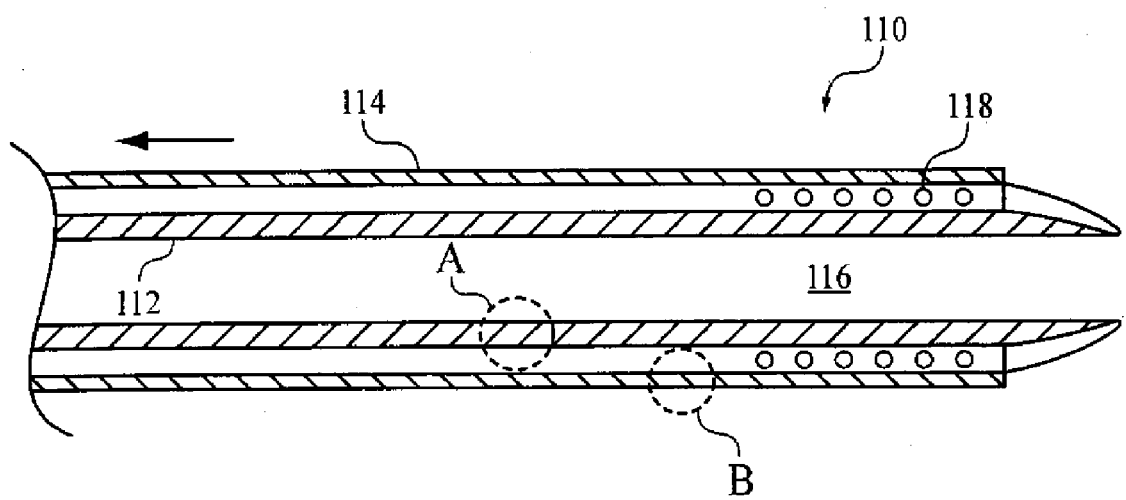
FIG. 8A is a cross-sectional side view of a portion of a stent delivery system.
Figure 8B:
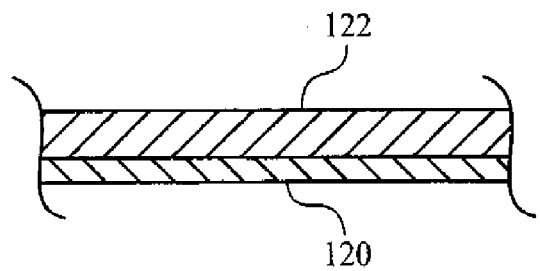
FIG. 8B is an enlarged view of region A in FIG. 8A.
Figure 8C:
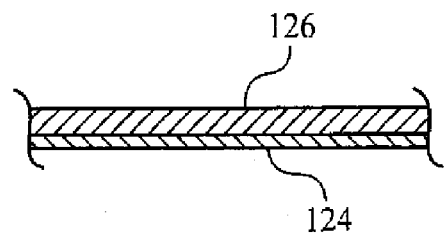
FIG. 8C is an enlarged view of region B in FIG. 5A.

Referring to FIG. 5A, a stent delivery system 110 includes an inner catheter 112 and a retractable sheath 114. Inner catheter 112 is a tube having a lumen 116 sized for delivery over a guidewire. A stent 118 is carried on a distal portion of inner catheter 112. Sheath 114 covers stent 118 during delivery and can be retracted to expose the stent for expansion at a treatment location within a body lumen such as a blood vessel. Inner catheter 112 and sheath 114 are coextruded members having at least two layers. Referring particularly to FIG. 8B, the inner catheter includes an inner layer 120 and an outer layer 122. Inner layer 120 is formed of a relatively low friction polymer to facilitate delivery over a guidewire. Outer layer 122 includes a nanocomposite material. Referring particularly to FIG. 8C, sheath 114 also includes an inner layer 124 and an outer layer 126. Inner layer 124 is a low friction polymer that facilitates sliding motion over the stent during retraction of the sheath. Outer layer 126 includes a nanocomposite material. Examples of nanocomposite materials include polyamide 12, e.g., Nylon 12-based materials such as the RTP formulations described above. High dimensional uniformity of the nanocomposite-containing coextruded catheter and sheath facilitates smooth delivery over the guidewire and sheath retraction. In embodiments, only the sheath or the inner catheter includes a nanocomposite material. A suitable stent is a self-expanding or balloon-expandable stent. In the case of a balloon-expandable stent, the stent is carried over a balloon mounted on the inner catheter. Further discussion of a delivery system for a self-expanding stent is described in Raeder-Devens et al., U.S. Patent Pub. No. 2003/0050686, the entire disclosure of which is hereby incorporated by reference.

The following examples are illustrative and not intended to be limiting.

Example I

A tube having three concentric layers (inner layer, middle layer, and outer layer) was co-extruded using cross-head 100 (FIGS. 4A-4B) in combination with an extrusion line that included three extruders arranged upstream of cross-head 100. Materials for the inner and outer layers were fed from the inner and outer extruders into respective gear pumps melt filters. The middle layer material was fed from the middle extruder into a melt filter. From the respective melt filters, the materials were each fed into separate adapters that fed into the cross-head 100. After extrusion of the three-layered tube from cross-head 100, the tube passed into a water tank about 6 feet long to cool the tube. After cooling, the tube was passed through an air wipe that removed water from the tube. The tube was pulled through the tank and the air wipe with a puller that regulated line speed. Subsequent to cooling and drying, the puller fed the tube into a cutter that cut the tube to a desired length.

The tube included an Ube Nano-PA 12, formula number #3030C2 (a nanocomposite material) outer layer, a Plexar® PX380 (a maleic anhydride polyolefin) middle layer, and a Marlex® 4903 (a high density polyethylene) inner layer. The materials selected for the outer, middle and inner layers were selected to provide high precision co-extrusion. In accordance with the selection criteria described above, the viscosity of the outer layer (the nanocomposite layer) at a shear rate of 1 s$^{-1}$ and a temperature of 220° C. was 2,750 Pa-s, which is within 25% to 120% of the viscosity value of the middle layer at 1 s$^{-1}$ and 220° C., 3,500 Pa-s), as shown in FIG. 4. In addition, the viscosity of the middle layer at a shear rate of 1 s$^{-1}$ and a temperature of 220° C. (3,500 Pa-s) was within 5% to 35% of the viscosity of the inner layer at 1 s$^{-1}$ and 220° C. (10,500 Pa-s), as shown in FIG. 4. In this example, the inner layer and the outer layer have different Theological properties (i.e., the inner layer has a viscosity that is at least three times greater than the viscosity of the outer layer at a shear rate or below about 1 s$^{-1}$ and a temperature of 220° C.)

The tube was co-extruded using the process temperatures and equipment shown in Table 1.

TABLE 1

| Material | Screw Diameter | Feed Temp. | Zone 1 Temp. | Zone 2 Temp. | Zone 3 Temp. | Extruder Clamp Temp. | Screen |
|---|---|---|---|---|---|---|---|
| Marlex® 4903 | ¾" meter | 70° F. | 345° F. | 365° F. | 385° F. | 420° F. | 60/100/60 |
| Plexar® 380 | ½" meter | 70° F. | 370° F. | 380° F. | 410° F. | 420° F. | None |

TABLE 1-continued

| Material | Screw Diameter | Feed Temp. | Zone 1 Temp. | Zone 2 Temp. | Zone 3 Temp. | Extruder Clamp Temp. | Screen |
|---|---|---|---|---|---|---|---|
| Ube Nano-PA12 | ¾" meter | 70° F. | 350° F. | 375° F. | 395° F. | 395° F. | 60/100/60 |

| Material | Barrel Pressure (psi) | Melt pump (cc/rev) | Pump Temp. | Melt Pump Speed (rpm) | Clamp Temp. | Filter | Filter Temp. | Adapter Temp | Heat Inlet Pressure (psi) |
|---|---|---|---|---|---|---|---|---|---|
| Marlex® 4903 | 1400 | 0.16 | 420° F. | 3.1 | 420° F. | 55 micron | 420° F. | 420° F. | 2300 |
| Plexar® PX380 | 1300 | None | None | None | None | 55 micron | 420° F. | 420° F. | 1600 |
| Ube Nano-PA12 | 1500 | 0.16 | 395° F. | 4.9 | 395° F. | 10 micron | 395° F. | 395° F. | 1725 |

Using a 0.048-inch die and a 0.032-inch mandrel/tip, the shape of the tube at the exit of cross-head 100 was formed. The line speed was about 37 feet per minute and the gap between the cross-head 100 and the water tank was 5/16". The temperature of cross-head 100 was 420° F. during extrusion. The air pressure was about 11 inches of water.

Each layer in the co-extruded tube was well-defined as viewed in cross-section with concentricity of the layers determined from four measurements equally distributed around the circumference. The outer layer formed about 53.6% of the cross-sectional area, the inner layer formed about 32.1% of the cross-sectional area, and the middle layer formed about 14.3% of the cross-sectional area. Calculated over the sampling (i.e., thickness measurements taken at 10 randomly selected, non-consecutive cross-sections over 1000 feet of product), the average wall thickness of the outer layer was 0.0015 inches, with a standard deviation of $3.0675 \times 10^{-5}$ inches over the duration of the run. The minimum value measured for the outer layer was 0.0015 inches and the maximum value measure for the outer layer was 0.0016 inches. The average wall thickness of the middle layer was 0.0004 inches, with a standard deviation of $4.0593 \times 10^{-5}$ inches over the duration of the run. The minimum value measured for the middle layer was 0.0003 inches and the maximum value measure for the middle layer was 0.0005 inches. The average wall thickness of the inner layer was 0.0009 inches, with a standard deviation of $7.0949 \times 10^{-5}$ inches over the duration of the run. The minimum value measured for the inner layer was 0.0008 inches and the maximum value measure for the inner layer was 0.0010 inches.

Example II

A tube having three concentric layers was co-extruded using the cross-head and extrusion line described in Example I. The outer layer of the tube was formed of RTP formula number 0299 FX 83107C (a nanocomposites material), a middle tie layer formed of Plexar® PX380 (a modified polyolefin), and an inner layer formed of Marlex® 4903 (a high density polyethylene). The materials for each of the layers were selected in accordance with the high precision co-extrusion criteria described above. For example, as shown in FIG. 4, at a shear rate of 1 $s^{-1}$ and a temperature of 220° C., RTP formula number 0299 FX 83107C has a viscosity of 1,200 Pa-s, which is within 25% to 120% of the viscosity of Plexar® PX380 at the same low shear rate and temperature, 3,500 Pa-s.

The tube was co-extruded using the process temperatures and equipment shown in Table 2.

TABLE 2

| Material | Screw Diameter | Feed Temp. | Zone 1 Temp. | Zone 2 Temp. | Zone 3 Temp. | Extruder Clamp Temp. | Screen |
|---|---|---|---|---|---|---|---|
| Marlex® 4903 | ¾" meter | 90° F. | 380° F. | 400° F. | 410° F. | 420° F. | 60/100/60 |
| Plexar® PX380 | ½" meter | 77° F. | 345° F. | 365° F. | 385° F. | 420° F. | None |
| RTP, 0299 FX 83107C | ¾" meter | 90° F. | 335° F. | 350° F. | 375° F. | 385° F. | 60/100/60 |

| Material | Barrel Pressure (psi) | Melt pump (cc/rev) | Pump Temp. | Melt Pump Speed (rpm) | Clamp Temp. | Filter | Filter Temp. | Adapter Temp | Head Inlet Pressure (psi) |
|---|---|---|---|---|---|---|---|---|---|
| Marlex® 4903 | 1650 | 0.16 | 420° F. | 3.0 | 420° F. | 55 micron | 420° F. | 420° F. | 1650 |
| Plexar® PX380 | 1000 | None | None | None | None | 55 micron | 410° F. | 410° F. | 1070 |
| RTF, 0299 FX 83107C | 1600 | 0.16 | 385° F. | 5.0 | 385° F. | 10 micron | 395° F. | 385° F. | 1060 |

Using a 0.042-inch die and a 0.028-inch mandrel/tip, the shape of the tube at the exit of cross-head 100 was formed. The line speed was about 39 feet per minute and the gap between the cross-head 100 and the water tank was ¼". The temperature of cross-head 100 was 410° F. during extrusion. The air pressure was about 17 inches of water.

Each layer in the co-extruded tube was well-defined as viewed in cross-section with concentricity of the layers determined from four measurements equally distributed around the circumference. The outer layer formed about 50% of the cross-sectional area, the inner layer formed about 32.1% of the cross-sectional area, and the middle layer formed about 17.9% of the cross-sectional area. Calculated over the sampling, the average wall thickness of the outer layer was 0.0014 inches, with a standard deviation of $3.5404 \times 10^{-5}$ inches over the duration of the run. The minimum value measured for the outer layer was 0.0014 inches and the maximum value measure for the outer layer was 0.0015 inches. The average wall thickness of the middle layer was 0.0005 inches, with a standard deviation of $3.9000 \times 10^{-5}$ inches over the duration of the run. The minimum value measured for the middle layer was 0.0004 inches and the maximum value measure for the middle layer was 0.0005 inches. The average wall thickness of the inner layer was 0.0009 inches, with a standard deviation of $4.5177 \times 10^{-5}$ inches over the duration of the run. The minimum value measured for the inner layer was 0.0009 inches and the maximum value measure for the inner layer was 0.0010 inches.

With regard to Examples I and II, in other embodiments, a tube can be formed to have a cross-sectional area that is composed of at least 30% of outer layer 24, at least 5% of middle layer 26, and at least 10% of inner layer 28.

All of the features disclosed herein may be combined in any combination. Each feature disclosed may be replaced by an alternative feature serving the same, equivalent, or similar purpose. Thus, unless expressly stated otherwise, each feature disclosed is only an example of a generic series of equivalent or similar features.

All publications, applications, and patents referred to in this application are herein incorporated by reference to the same extent as if each individual publication or patent was specifically and individually indicated to be incorporated by reference in their entirety.

Other embodiments are within the claims.

What is claimed is:

1. A method of manufacturing a device including a first layer, a second layer and a third layer, the method comprising:
    selecting a material for the second layer, the material having a viscosity value at a shear rate of about $1\ s^{-1}$ or less and at a selected temperature;
    selecting a nanocomposite material for the first layer that has a viscosity within about 20% to about 125% of the viscosity value of the material for the second layer, wherein the nanocomposite material includes a polymer matrix having dispersed therein nanosized particles having a size of from 1 nm to 1000 nm;
    selecting a material for the third layer, the third material being selected such that the viscosity of the second material is between about 5 percent and about 35 percent of a viscosity of the third material;
    co-extruding the first, second and third layers.

2. The method of claim 1, wherein the device comprises a medical device.

3. The method of claim 1, wherein the device comprises a catheter.

4. The method of claim 1, wherein the shear rate is below about $0.5\ s^{-1}$.

5. The method of claim 1, wherein the shear rate is about $0.1\ s^{-1}$.

6. The method of claim 1, wherein the selected temperature is about 60° C. to about 120° C. above a flow temperature of a highest flow temperature material co-extruded.

7. The method of claim 1, wherein the device is a medical device, the method comprising:
    forming a tubular member, the tubular member comprising the first layer, the second layer and the third layer co-extruded with the first layer, and one of the layers comprises a thickness that varies by less than about 20% from a mean value of thickness, the thickness being measured at four points per cross-sectional cut made at ten random, non-consecutive locations along a production length of the tubular member; and
    incorporating a portion of the tubular member as a component of the medical device.

8. The method of claim 7, wherein the medical device is a catheter.

9. The method of claim 7, wherein the medical device is a balloon-catheter.

10. The method of claim 7, wherein the thickness varies by less than 15% from the mean value of thickness.

11. The method of claim 7, wherein the thickness varies by less than 10% from the mean value of thickness.

12. A high precision method of manufacturing a medical device having a three-layer elongate shaft, the method comprising the steps of:
    providing a first material that will form an outer layer of the elongate shaft, the first material comprising a nanocomposite material having a first viscosity measured at a shear rate of $1\ s^{-1}$ and a temperature of 220° C., wherein the nanocomposite material includes a polymer matrix having dispersed therein nanosized particles having a size of from 1 nm to 1000 nm;
    providing a second material that will form a middle layer of the elongate shaft, the second material comprising a polyolefin having a second viscosity measured at a shear rate of $1\ s^{-1}$ and a temperature of 220° C.;
    providing a third material that will form an inner layer of the elongate shaft, the third material comprising a high density polyethylene having a third viscosity measured at a shear rate of $1\ s^{-1}$ and a temperature of 220° C.; and
    co-extruding the first material, the second material and the third material to form the three-layer elongate shaft;
    wherein the first viscosity has a value that is between 25 percent and 125 percent of the second viscosity and the second viscosity is between 5 percent and 35 percent of the third viscosity.

13. The method of claim 12, wherein providing a first material comprises providing a first material having a first viscosity, measured at a shear rate of $1\ s^{-1}$ and a temperature of 220° C., of about 2,750 Pa·s.

14. The method of claim 12, wherein providing a first material comprises providing a first material having a first viscosity, measured at a shear rate of $1\ s^{-1}$ and a temperature of 220° C., of about 1,200 Pa·s.

15. The method of claim 12, wherein providing a second material comprises providing a second material having a second viscosity, measured at a shear rate of $1\ s^{-1}$ and a temperature of 220° C., of about 3,500 Pa·s.

16. The method of claim 12, wherein providing a third material comprises providing a third material having a third viscosity, measured at a shear rate of $1\ s^{-1}$ and a temperature of 220° C., of about 10,500 Pa·s.

17. The method of claim 12, wherein providing a first material comprises providing a first material comprising nanosized particles dispersed within a polyamide.

18. The method of claim 12, wherein providing a second material comprises providing a second material comprising a maleic anhydride polyolefin.

* * * * *